United States Patent [19]

Sleevi et al.

[11] Patent Number: 5,382,596
[45] Date of Patent: Jan. 17, 1995

[54] SUBSTITUTED 2-AMINOTETRALINS

[75] Inventors: Mark C. Sleevi, Midlothian; Gevork Minaskanian, Richmond; L. Meredith Moses, Glen Allen, all of Va.

[73] Assignee: Discovery Therapeutics, Inc., Richmond, Va.

[21] Appl. No.: 102,436

[22] Filed: Aug. 5, 1993

[51] Int. Cl.⁶ .................... A61K 31/35; A61K 31/36; A61K 31/135; C07D 315/00; C07D 317/70; C07D 211/00
[52] U.S. Cl. .................... 514/459; 514/466; 514/471; 514/657; 549/426; 549/433; 549/451; 564/428
[58] Field of Search .................... 549/426, 433, 451; 564/428; 514/459, 466, 471, 657

[56] References Cited

U.S. PATENT DOCUMENTS

| | | | |
|---|---|---|---|
| 3,296,249 | 1/1967 | Bell | 260/239.3 |
| 3,930,022 | 12/1975 | Hauck et al. | 424/330 |
| 3,991,207 | 11/1976 | Sarges et al. | 424/319 |
| 4,010,202 | 3/1977 | Sugihara et al. | 260/573 |
| 4,035,512 | 7/1977 | Sugihara et al. | 424/330 |
| 4,057,582 | 11/1977 | Dunnigan et al. | 260/574 |
| 4,076,843 | 2/1978 | Hauck et al. | 424/330 |
| 4,267,373 | 5/1981 | Hauck et al. | 564/428 |
| 4,410,519 | 10/1983 | Seiler et al. | 424/226 |
| 4,564,628 | 1/1986 | Horn | 514/438 |
| 4,722,933 | 2/1988 | Horn | 514/438 |
| 5,068,325 | 11/1991 | Grell et al. | 514/215 |

FOREIGN PATENT DOCUMENTS 0321968 6/1989 European Pat. Off. .
2333847 1/1974 Germany .

OTHER PUBLICATIONS

Santangelo et al, CA 120(9)=106565z (1993).
Hook et al, CA 120(1)=8264f (1993).
Peck et al, CA 115(3)=28926y (1991).
Horn, CA 111(1)=753h (1988).
Chiesi et al, CA 100(23)=191603q (1983).
Cannon et al, J. Med. Chem. 24(2), 149–53 (1981)—only Chem Abst. is provided.
McDermed et al. *J. Med. Chem.*, 18(4), 362–367 (1975).
McDermed et al., *J. Med. Chem.*, 19(4), 547–549 (1976).
Hacksell et al., *J. Med. Chem.*, 22(12), 1469–1475 (1979).
Seiler et al., *J. Med. Chem.*, 29, 912–917 (1986).
Munson et al., *Analytical Biochemistry*, 107, 220–239 (1980).

*Primary Examiner*—Cecilia Tsang
*Attorney, Agent, or Firm*—Sterne, Kessler, Goldstein & Fox

[57] ABSTRACT

Optically active or racemic compounds represented by the formula

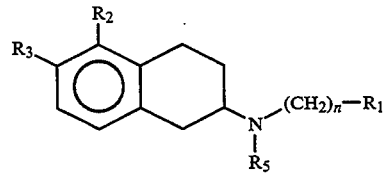

where $R_2$ is OA and $R_3$ is selected from the group consisting of H and OA; where A is H or is selected from the group consisting of hydrocarbyl radicals comprising between 1 and 3 carbon atoms, as well as

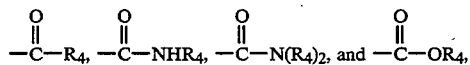

with the proviso that when $R_3$ is OA, then $R_2$ and $R_3$ may be bonded together to form the group

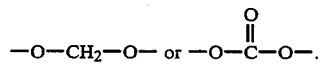

$R_4$ is selected from the group consisting of alkyl and aromatic residues having from 1 to 20, preferably from 1 to 12, carbon atoms, for example, alkyl, optionally substituted with aromatic residues, and aromatic residues optionally substituted with alkyl radicals; n is an integer from 1 to 4; $R_5$ is an unbranched alkyl chain (Abstract continued on next page.)

ABSTRACT comprising from 1 and 3 carbon atoms or a cyclopropylmethyl radical; $R_1$ is alkoxy, cycloalkoxy and a cyclic ether of the formula

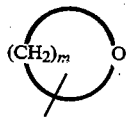

where m is an integer from 3 to 5; with the proviso that when $R_1$ is alkoxy, then $R_3$ cannot be H; and pharmaceutically-acceptable salts thereof.

These compounds are useful for alleviating Parkinsonism, glaucoma, hyperprolactinemia and for inducing weight loss in mammals.

21 Claims, No Drawings

SUBSTITUTED 2-AMINOTETRALINS

FIELD OF THE INVENTION

This invention relates generally to substituted 2-aminotetralins, to processes for preparing such compounds and methods for administering compositions of such compounds in amounts effective to induce a desired physiological response in mammals. More particularly, the invention relates to compounds for therapeutic use, in particular in treating central nervous, endocrine and ophthalmic disorders. The compounds of this invention are useful for alleviating Parkinsonism, glaucoma, hyperprolactinemia, and for inducing weight loss in mammals.

BACKGROUND OF THE INVENTION

It is known that various hydroxylated 2-aminotetralins of the general formula

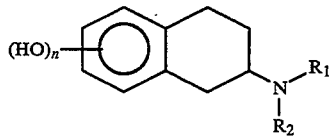

where $R_1$ and $R_2$ are saturated alkyl groups and n is 1 or 2, are dopamine receptor agonists [McDermed et al., J. Med. Chem. 18, 362 (1975); McDermed et al., J. Med. Chem. 19, 547 (1976); Hacksell et al., J. Med. Chem. 22, 1469 (1979)].

It is also known that compounds where n is 1, $R_1$ is a saturated alkyl group, and $R_2$ is various functionalized alkyl groups have been shown to be dopamine receptor agonists [Seiler et al., U.S. Pat. No. 4,410,519; Seiler et al., J. Med. Chem. 29, 912 (1986) ].

Horn, in U.S. Pat. No. 4,564,628, has disclosed that various hydroxylated 2-aminotetralins with aralkyl substituents are useful as dopamine and D-2 receptor agonists for the treatment of disorders of the central nervous system as applied to Parkinson's disease and related disorders, hypertension and hyperprolactinemia.

U.S. Pat. No. 4,722,933 further discloses that certain aralkyl substituted 2-aminotetralins are useful in lowering intraocular pressure in mammals and can be beneficial for alleviating the symptoms of glaucoma.

Santangelo, in European Patent Application No. 0321968, describes certain aminotetralins with aryloxyalkyl substituents as having cardiovascular activity.

The need exists for more and better drugs useful in the treatment of central nervous, ophthalmic and endocrine disorders in humans and other animals. Especially, the need exists for drugs that cause a minimum of undesirable side effects at therapeutic dosages and for drugs that do not show tolerance in the subject upon prolonged administration, but are capable of advantageously affecting the dopamine receptor sites without providing an undesirable physiological response.

SUMMARY OF THE INVENTION

There has now been discovered certain novel compounds having dopaminergic activity and having the structural formula

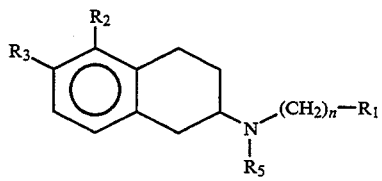

where $R_2$ is OA and $R_3$ is selected from the group consisting of H and OA; where A is H or is selected from the group consisting of hydrocarbyl radicals comprising between 1 and 3 carbon atoms, as well as

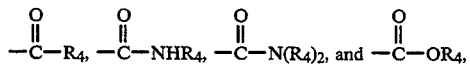

with the proviso that when both $R_2$ and $R_3$ are OA, then $R_2$ and $R_3$ may be bonded together to form the group

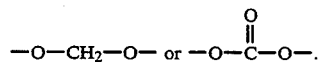

$R_4$ is selected from the group consisting of alkyl and aromatic residues having from 1 to 20, preferably from 1 to 12, carbon atoms, for example, alkyl, optionally substituted with aromatic residues, and aromatic residues optionally substituted with alkyl radicals; n is an integer from 1 to 4; $R_5$ is an unbranched alkyl chain having from 1 to 3 carbon atoms or a cyclopropylmethyl radical; and $R_1$ is alkoxy, cycloalkoxy and a cyclic ether of the formula

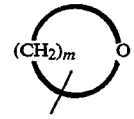

where m is an integer from 3 to 5; with the provision that when $R_1$ is alkoxy, then $R_3$ cannot be H.

It is essential that the compounds in the present invention be an optically active compound or racemic mixture thereof having substantial affinity and selectivity for binding to dopamine D-2 receptors, e.g. in a human.

DESCRIPTION OF PREFERRED EMBODIMENTS

Alkyl means straight or branched hydrocarbon alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl;

Alkoxy means straight-chain or branched hydrocarbon alkoxy having 1 to 5 carbon atoms and includes, for example, methoxy, ethoxy, propoxy, isopropoxy, butoxy, iso-butoxy, secondary butoxy, tertiary butoxy, pentyloxy, and isopentyloxy;

Cycloalkoxy means that the cycloalkyl moiety is a cyclic alkyl group having 3 to 5 carbon atoms;

Aromatic residues means phenyl or naphthyl or substituted phenyl or substituted naphthyl which are phenyl or naphthyl substituted by at least one substituent selected from the group consisting of halogen (chlorine, bromine, fluorine or iodine), amino, nitro, hydroxy, and alkyl.

It should be noted that the term "hydrocarbyl" includes both the above-defined alkyl and aromatic residues.

Further, the group —$(CH_2)_n$—, as shown in the structural formula of the compounds of the present invention, includes both linear and branched moieties.

The compounds used in the present invention are selected from the group of stereoisomers or mixtures thereof of compounds having dopaminergic activity represented by the formula

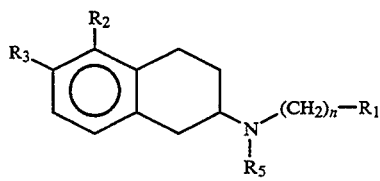

where $R_2$ is OA and $R_3$ is selected from the group consisting of H and OA; where A is H or is selected from the group consisting of hydrocarbyl radicals comprising between 1 and 3 carbon atoms, as well as

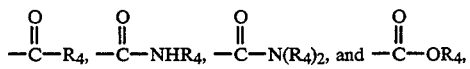

with the proviso that when $R_3$ is OA, then $R_2$ and $R_3$ may be bonded together to form the group

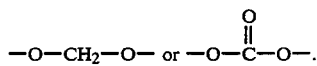

$R_4$ is selected from the group consisting of alkyl and aromatic residues having from 1 to 20, preferably from 1 to 12, carbon atoms, for example, alkyl, optionally substituted with aromatic residues, and aromatic residues optionally substituted with alkyl radicals; n is an integer from 1 to 4; $R_5$ is an unbranched alkyl chain comprising from 1 and 3 carbon atoms or a cyclopropylmethyl radical; $R_1$ is alkoxy, cycloalkoxy and a cyclic ether of the formula

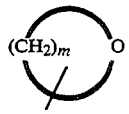

where m is an integer from 3 to 5; with the proviso that when $R_1$ is alkoxy, then $R_3$ cannot be H; and pharmaceutically-acceptable salts thereof.

Preferably, $R_3$ is OA and A is H, and more preferably $R_4$ is an alkyl or aryl radical, for example, methyl, t-butyl, pentyl, nonyl, undecyl, or phenyl.

The more preferred groups represented by $R_1$ are ethoxy, propoxy, isopropoxy, butoxy, s-butoxy, isobutoxy, and t-butoxy.

In the more preferred compounds for use in the present invention, n is 2 or 3 and $R_3$ is OA; and most preferably A is H, $R_5$ is propyl, and the stereochemical configuration of the carbon atom in the tetralin ring bearing nitrogen is S.

It is essential that the compounds herein be an optically active or racemic mixture capable of binding selectively to dopamine D-2 receptors, e.g., in a human.

In particular, (S)-6-[[2-(1,1-dimethylethoxy)ethyl]propylamino]-5,6,7,8-tetrahydro-1,2-naphthalenediol is an especially preferred compound because of its high affinity, selectivity, specificity, and functional potency at dopamine D-2 receptors, as well as its high in vivo functional potency. Due to their pharmacological profile, it is believed that the compounds herein will be useful in the treatment of central nervous, ophthalmic, and endocrine disorders. In particular, it is believed that the compounds herein are useful in the treatment of such conditions in humans as Parkinsonism, elevated intraocular pressure, and for inducing weight loss in humans and other mammals.

Particularly preferred compounds are as follows: (S)-5,6,7,8-tetrahydro-6-[[2-(1-methylethoxy) ethyl]propylamino]-1,2-naphthalenediol, (S)-6-[[2-(ethoxy)ethyl]propylamino]-5,6,7,8- tetrahydro-1,2-naphthalenediol, (S)-5,6,7,8-tetrahydro-6-[[2-(propoxy)ethyl]propylamino]-1,2-naphthalenediol, (S)-6-[[2-(butoxy)ethyl]propylamino]-5,6,7,8-tetrahydro-1,2-naphthalenediol, (S)-6-[[2-(1,1-dimethylethoxy)ethyl]propylamino]-5,6,7,8-tetrahydro-1,2-naphthalenedio, (6S)-5,6,7,8-tetrahydro-6-[[(tetrahydro-3-furanyl)methyl]propylamino]-1-naphthalenol, (S)-6,7,8,9-tetrahydro-N-[2-(1-methylethoxy)ethyl]-N-propylnaphtho[1,2-d]-1,3-dioxol-7-amine, (S)-5,6,7,8-tetrahydro-6-[[2-(1methylethoxy)ethyl]propylamino]-1,2-naphthalenediol diacetate, (S)-5,6,7,8-tetrahydro-6-[[2-(1-methylethoxy)ethyl]propylamino]-1,2-naphthalenediol dihexanoate, (S)-5,6,7,8-tetrahydro-6-[[2-(1-methylethoxy) ethyl]propylamino]-1,2-naphthalenediol cyclic carbonate, and (S)-6-[[2-(1,1-dimethylethoxy)ethyl]propylamino]-5,6,7,8-tetrahydro-1,2-naphthalenediol diacetate.

Methods for preparing the S-enantiomers of the compounds of the present invention employ S-5-methoxy-2-n-propylaminotetralin disclosed in U.S. Pat. No. 4,968,837, or S-5-methoxy-2-aminotetralin disclosed in McDermed, et. al., J. Med. Chem. 19(4), 547–9 (1976), which are hereby incorporated by reference.

For purposes of this invention, designation of the S-enantiomer shall mean that the S-enantiomer is present in excess of the R-enantiomer. Preferably, the mixture is greater than 90 mole-percent of the S-enantiomer. Most preferably, the S-enantiomer is substantially pure, i.e., greater than 99 mole-percent.

This invention provides a method of treatment which comprises inducing a response at D-2 receptors by administering a therapeutically-effective amount of one of the foregoing compounds to the patient. In general, a pharmacologically-effective daily dose can be from 0.001 mg./kg. to 100 mg./kg. per day, and preferably from about 0.005 mg./kg. to 10 mg./kg. per day, bearing in mind, of course that in selecting the appropriate dosage, in any specific case, consideration must be given to the patient's weight, general health, metabolism, age, and other factors which influence response to the drug. A particularly preferred dose is 0.005 mg./kg. (subcutaneous) per day.

Another embodiment of this invention is the provision of pharmaceutical compositions in dosage unit form which comprise from about 0.05 to 500 mg. of a compound of the above formula.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, antioxidants, and preserving agents in order to provide a pharmaceutically elegant and palatable preparation. Tablets contain the active ingredient in admixture with non-toxic pharmaceutically-acceptable excipients which are suitable for manufacture of tablets. These excipients may be, for example, inert diluents, for example, calcium carbonate, sodium carbonate, lactose, calcium phosphate, or sodium phosphate; granulating and disintegrating agents, for example, maize starch, or alginic acid; binding agents, for example, starch, gelatin, or acacia; and lubricating agents, for example, magnesium stearate, stearic acids, or talc. The tablets may be uncoated or they may be coated by known techniques to delay disintegration and adsorption in the gastrointestinal tract and thereby provide a sustained action over a longer period.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with an oil medium, for example, arachis oil, liquid paraffin, or olive oil.

Aqueous suspensions contain the active compound in admixture with excipients suitable for the manufacture of aqueous suspensions. Such excipients are suspending agents, for example, sodium carboxymethylcellulose, methylcellulose, hydroxypropylmethylcellulose, sodium alginate, polyvinylpyrrolidone, gum tragacanth, and gum acacia; dispersing or wetting agents may be naturally-occurring phosphatides, for example, lecithin, or condensation products of an alkylene oxide with fatty acids, for example polyoxyethylene stearate, or condensation products of ethylene oxide with long chain aliphatic alcohols, for example, heptadecethyleneoxycycetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example, polyoxyethylene sorbitan monooleate. The aqueous suspensions may also contain one or more preservatives, for example, ethyl-, n-propyl-, or p-hydroxybenzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents may also be present.

Syrups and elixirs may be formulated with sweetening agents, for example, glycerol, sorbitol or sucrose. Such formulations may also contain a demulcent, preservative, flavoring or coloring agent. The pharmaceutical compositions may be in the form of a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butanediol.

The pharmaceutical compositions may be tableted or otherwise formulated so that for every 100 parts by weight of the composition there are present between 5 and 95 parts by weight of the active ingredient. The dosage unit form will generally contain between about 0.05 mg. and about 100 mg. of the active ingredient of the formula stated above.

From the foregoing formulation discussion, it is apparent that the compositions of this invention can be administered orally or parenterally. The term parenterally as used herein includes subcutaneous injection, intravenous, intramuscular, or intrasternal injection or fusion techniques. The compositions can also be administered transdermally with the optional use of a transdermal penetration enhancer such as Azone ® (as described in U.S. Pat. No. 4,405,616) in a variety of formulations such as patches, topical creams, or solutions as well known in the art.

To illustrate the manner in which the invention may be carried out, the following examples are given. It is understood, however, that the examples are for the purpose of illustration and the invention is not to be regarded as limited to any of the specific materials or conditions therein.

EXAMPLES

Compounds of the present invention wherein $R_2$ and $R_3$ are both OH (general formula 1) can be prepared as shown below (Method A). The process is described in detail for Example #1. For all the following methods, the required triflates [$R_6OSO_2CF_3$, wherein $R_6$ is defined as $R_1-(CH_2)_n-$] are prepared in situ from alcohols obtained commercially or available by methods previously published in the literature.

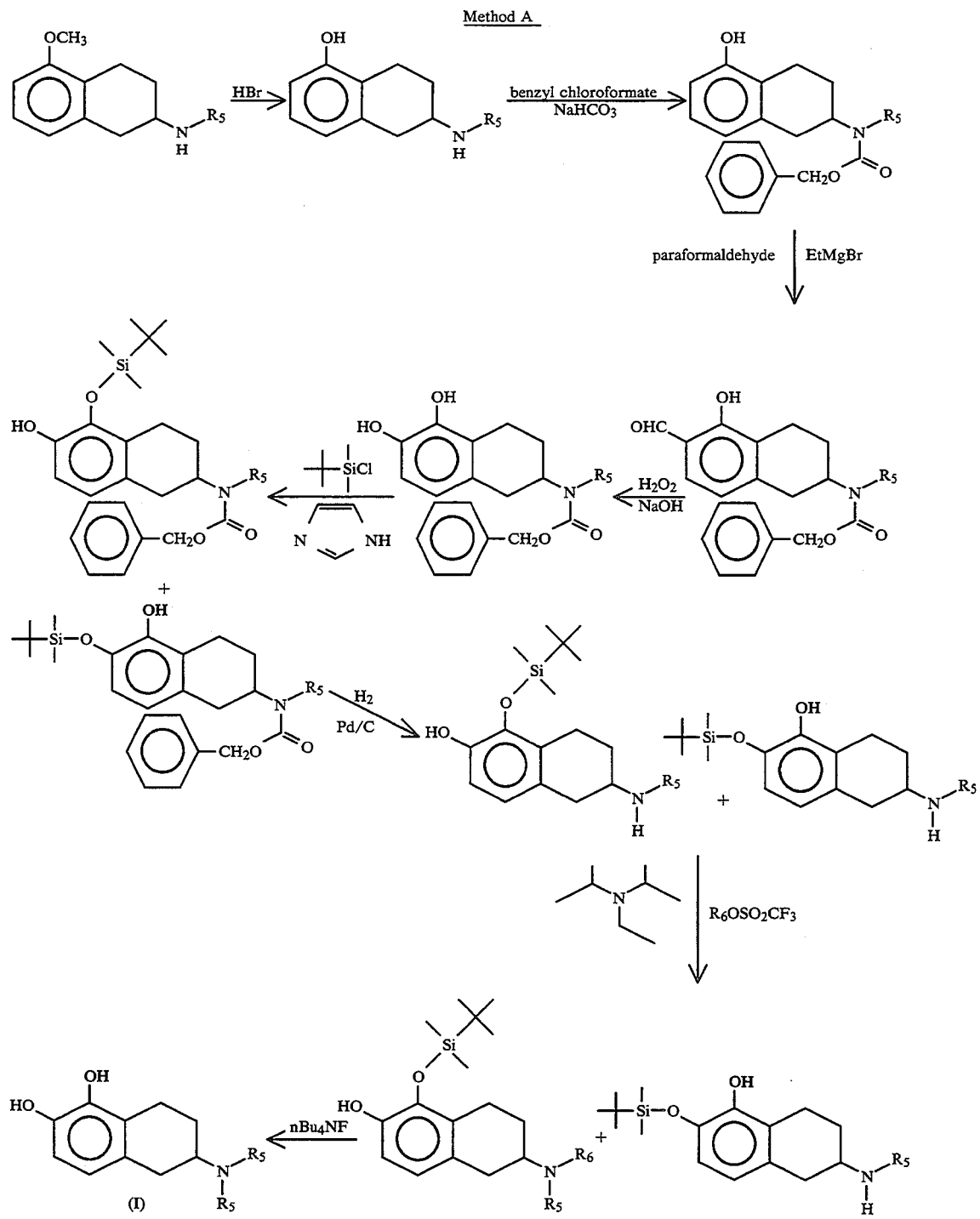

Method A

Method A - Detailed Example

Preparation of
(S)-5,6,7,8-tetrahydro-6-[[2-(1-methylethoxy)-ethyl]-propylamino]-1,2-naphthalenediol, hydrochloride
(Example 1)

A.

(S)-5,6,7,8-Tetrahydro-6-propylamino-1-naphthalenol, hydrobromide.

A mixture of (S)-1,2,3,4-tetrahydro-5-methoxy-N-propyl-2-naphthalenamine (10.0 g, 0.0391 mol) as the HCl salt, or its corresponding free base, was heated at reflux in 48% hydrobromic acid (150 mL) for a period of two to three hours. The solution was cooled to room temperature and the resulting solid was collected by filtration. Drying under high vacuum at 60° C. gave 10.7 g of the product (96% yield).

B.

(S)-N-(1,2,3,4-Tetrahydro-5-hydroxy-2-naphthalenyl)-N-propylcarbamic acid, phenylmethyl ester.

A stirring suspension of (S)-6-propylamino-5,6,7,8-tetrahydro-1-naphthalenol (7.34 g, 0.0257 mol) in water (100 mL) was cooled in an ice bath and sodium bicarbonate (8.49 g, 0,101 mol) was added. This suspension was stirred for fifteen minutes then benzyl chloroformate (4.50 g, 0.0264 mol) was added dropwise. The mixture was stirred for fifteen minutes and then allowed to come to room temperature. Ether (100 mL) was added and the mixture was stirred overnight. The layers were separated and the aqueous layer was extracted with ether. The combined organic layers were washed twice with saturated aqueous sodium bicarbonate, once with water, twice with dilute hydrochloric acid, once with water and once with saturated aqueous sodium chloride, dried (magnesium sulfate) and concentrated under reduced pressure to give 7.09 g (81% yield) of product as a yellow solid.

C.

(S)-N-(6-Formyl-1,2,3,4-tetrahydro-5-hydroxy-2-naphthalenyl)-N-propylcarbamic acid, phenylmethyl ester.

A solution of (S)-N-(1,2,3,4-tetrahydro-5-hydroxy-2-naphthalenyl)-N-propylcarbamic acid, phenylmethyl ester (7.09 g, 0.0209 mol) in dry toluene (400 mL) was stirring under a nitrogen atmosphere at room temperature and ethylmagnesium bromide (7.3 mL of a 3.0M solution in ether, 0.0219 mol) was added. The suspension was stirred for fifteen minutes and then a portion of the solvent (50 mL) was removed by distillation. After the suspension was cooled to room temperature, para-formaldehyde (1.57 g, 0.0523 mol) was added, followed by hexamethylphosphoramide (3.75 g, 0.0209 mol). The solution was heated at reflux for three hours and poured into aqueous 1N hydrochloric acid (800 mL) with stirring. Ether was added and the layers were separated. The aqueous layer was extracted again with ether. The combined organic extracts were washed three times with water and once with saturated aqueous sodium chloride, dried (magnesium sulfate) and concentrated under reduced pressure. Column chromatography of the oily residue on silica eluting with ethyl acetate-light pet ether (1:4) afforded 6.96 g of product (91% yield).

D.

(S)-N-(1,2,3,4-Tetrahydro-5,6-dihydroxy-2-naphthalenlyl)-N-propylcarbamic acid, phenylmethyl ester.

A solution of (S)-N-(6-formyl-1,2,3,4-tetrahydro-5-hydroxy-2-naphthalenyl)-N-propylcarbamic acid, phenylmethyl ester (6.96 g, 0.0190 mol) in methanol (25 mL) was stirred at room temperature, then sodium hydroxide (19.0 mL of a 1N aqueous solution, 0.0190 mol) and water (25 mL) were added. A stream of nitrogen was bubbled through the solution for thirty minutes. Hydrogen peroxide (2.12 mL of a 30% aqueous solution, 0.0206 mol) was added dropwise and the mixture was stirred under nitrogen for ninety minutes. Aqueous 1N hydrochloric acid (16 mL) and ether were added. The layers were separated and the aqueous layer was extracted with ether. The combined organic layers were washed twice with water and once with saturated aqueous sodium chloride, dried (magnesium sulfate) and concentrated under reduced pressure. Recrystallization of the residue from ethyl acetate-light pet ether gave 5.29 g (78% yield) of product as a white solid.

E.

Mixture of (S)-N-[5-[dimethylethyl)silyloxy]-6-hydroxy-1,2,3,4-tetrahydro-2-naphthalenyl]-N-propylcarbamic acid and (S)-N-[6-[dimethyl(1,1-dimethylethyl)silyloxy]-5-hydroxy-1,2,3,4-tetrahydro-2-naphthalenyl]-N-propylcarbamic acid, phenylmethyl esters.

A solution of (S)-N-(5,6-dihydroxy-1,2,3,4-tetrahydro-2-naphthalenyl)-N-propylcarbamic acid, phenylmethyl ester (1.5 g, 0.00422 mol) in dry tetrahydrofuran (30 mL) was stirred under nitrogen and tert-butyldimethylsilyl chloride (1.40 g, 0.00929 mol) was added, followed by imidazole (1.44 g, 0.0212 mol). The suspension was stirred at room temperature overnight. Water and ether were added and the layers were separated. The aqueous layer was extracted twice with ether and the combined organic layers were washed once with water and once with saturated aqueous sodium chloride, dried (magnesium sulfate) and concentrated. Column chromatography of the oily residue on silica eluting with ethyl acetate-light pet ether (1:9) yielded 1.54 g (78% yield) of the product mixture as a colorless oil.

F.

Mixture of (S)-2-[dimethyl(1,1-dimethylethyl)silyloxyl]-6-propylamino-5,6,7,8-tetrahydro-1-naphthalenol and (S)-1-[dimethyl(1,1-dimethylethyl)silyloxy]-6-propylamino-5,6,7,8-tetrahydro-2-naphthalenol.

The mixture of (S)-N-[5-[dimethylethyl)silyloxy]-6-hydroxy-1,2,3,4-tetrahydro-2-naphthalenyl]-N-propylcarbamic acid and (S)-N-[6-[dimethyl(1,1-dimethylethyl)silyloxy]-5-hydroxy-1,2,3,4-tetrahydro-2-naphthalenyl]-N-propylcarbamic acid, phenylmethyl esters (1.54 g, 0.00328 mol) in tetrahydrofuran (50 mL) was hydrogenated (40 psi) over 5% palladium on carbon for two hours. The catalyst was removed by filtration through a pad of Celite. The filtrate was concentrated under reduced pressure to give the oily product mixture which was used without additional purification.

G.

Mixture of (S)-2-[dimethyl(1,1-dimethylethyl)silyloxy]-6-[[2-(1-methylethoxy)ethyl]propylamino]-5,6,7,8-tetrahydro-1-naphthalenol and (S)-1-[dimethyl((1,1-dimethylyl)silyloxy]-6-[2-(1-methylethoxy)ethyl]propylamino]-5,6,7,8-tetrahydro-2-naphthalenol.

A solution of 2-(1-methylethoxy)ethanol (0.49 g, 0.00471 mol) in methylene chloride (10 mL) was cooled in an ice-acetone bath with stirring under nitrogen. Diisopropylethylamine (1.2 g, 0.00928 mol) was added, followed by trifluoromethane-sulfonic anhydride (1.33 g, 0.00471 mol) and the solution was stirred for ten minutes. A solution of the mixture of (S)-2[dimethyl (1,1-dimethylethyl)silyloxy]-6-propylamino-5,6,7,8-tetrahydro-1-naphthalenol and (S)-1-[dimethyl(1,1-dimethyl-ethyl)silyloxy]-6-propylamino-5,6,7,8-tetrahydro-2-naphthalenol in methylene chloride (15 mL) was added dropwise. The solution was allowed to come to room temperature and stirred overnight. Water and ether were added and the layers were separated. The aqueous layer was extracted with ether and the combined organic layers were washed once with water and once with saturated aqueous sodium chloride, dried (magnesium sulfate) and concentrated. Column chromatography of the residue on silica eluting with ethyl acetate-light pet ether (1:9) gave 0.56 g (40% yield) of the product mixture as a colorless oil.

H. (S)-5,6,7,8-Tetrahydro-6-[[2-(1-methylethoxy)ethyl]propylamino]-1,2-naphthalenediol, hydrochloride.

The oily mixture of (S)-2-[dimethyl(1,1-dimethylethyl)silyloxy]-6-[[2-(1-methylethoxy)ethyl]propylamino]-5,6,7,8-tetrahydro-1-naphthalenol and (S)-1-[dimethyl((1,1-dimethylethyl)silyloxy]-6-[[2-(1-methylethoxy)ethyl]propylamino]-5,6,7,8-tetrahydro-2-naphthalenol (0.56 g, 0.00133 mol) was dissolved in dry tetrahydrofuran (50 mL) and a stream of nitrogen was bubbled through the stirring solution for twenty minutes. Tetrabutylammonium fluoride (3.92 mL of a 1.0M solution in tetrahydrofuran, 0.00392 mol) was added and the solution (with nitrogen still bubbling) was stirred at room temperature for forty-five minutes. Water and ether were added and the layers were separated. The aqueous layer was extracted with ether and the combined organic layers were washed twice with water and once with saturated aqueous sodium chloride, dried (magnesium sulfate) and concentrated. Column chromatography of the residue on silica eluting with ethyl acetate-light pet ether (1:1) afforded the oily free base of the product. This material was dissolved in ether and treated with ethereal hydrogen chloride. The mother liquor was decanted from the amorphous solid which separated and the solid was washed twice with additional ether. Drying under high vacuum at 40° C. overnight gave 0.2163 g (47% yield) of the product.

Table I summarizes compounds which are examples of the present invention prepared by Method A, in which $R_2$ and $R_3$ are both OH and $R_5$ is —$CH_2CH_2CH_3$:

TABLE I

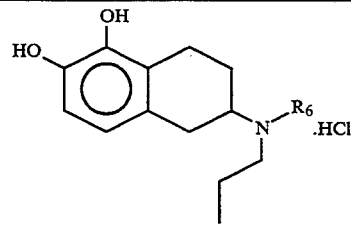

| Example | $R_6$ | Elemental Formula | Elemental Analysis (calc./obs.) | $[\alpha]_D$ (MeOH) |
|---|---|---|---|---|
| 1 | —$CH_2CH_2OCH(CH_3)_2$ | $C_{18}H_{30}NO_3$ Cl | C: 62.87/63.05<br>H: 8.79/8.83<br>N: 4.07/3.89 | −44.9<br>c = 1.1 |
| 2 | —$CH_2CH_2OCH_2CH_3$ | $C_{17}H_{28}NO_3$ Cl | C: 61.90/61.74<br>H: 8.56/8.50<br>N: 4.25/4.14 | −52.6<br>c = 0.82 |
| 3 | —$CH_2CH_2OCH_2$—◁ | $C_{19}H_{30}NO_3$ Cl | C: 64.12/64.10<br>H: 8.50/8.64<br>N: 3.94/3.84 | −51.8<br>c = 1.4 |
| 4 | —$CH_2CH_2OCH_3$ | $C_{16}H_{26}NO_3$ Cl | C: 60.85/60.89<br>H: 8.30/8.40<br>N: 4.43/4.30 | −57.4<br>c = 1.1 |
| 5 | —$(CH_2)_2OCH(CH_3)CH_2CH_3$ | $C_{19}H_{32}NO_3$ Cl | C: 63.76/63.91<br>H: 9.01/9.01<br>N: 3.91/3.89 | −52.1<br>c = 1.0 |
| 6 | —$CH_2CH_2O$—(cyclopentyl) | $C_{20}H_{32}NO_3$ Cl | C: 64.94/65.19<br>H: 8.72/8.60<br>N: 3.79/3.68 | −49.2<br>c = 1.1 |
| 7 | —$(CH_2)_2O(CH_2)_2CH_3$ | $C_{18}H_{30}NO_3$ Cl | C: 62.87/63.00<br>H: 8.79/8.99<br>N: 4.07/4.10 | −53.0<br>c = 1.4 |
| 8 | —$(CH_2)_2O(CH_2)_3CH_3$ | $C_{19}H_{32}NO_3$ Cl | C: 63.76/63.60<br>H: 9.01/9.11<br>N: 3.91/3.87 | −52.5<br>c = 1.1 |
| 9 | —$(CH_2)_2OC(CH_3)_3$ | $C_{19}H_{32}NO_3$ Cl | C: 63.76/63.80<br>H: 9.01/9.03<br>N: 3.91/4.03 | −50.1<br>c = 0.40 |
| 10 | —$(CH_2)_2O(CH_2)_4CH_3$ | $C_{20}H_{34}NO_3$ Cl | C: 64.58/64.70<br>H: 9.21/9.40<br>N: 3.77/3.97 | −51.7<br>c = 1.1 |
| 11 | —$CH_2CH_2$—(tetrahydrofuranyl) | $C_{19}H_{30}NO_3$ Cl | C: 64.12/63.85<br>H: 8.50/8.69<br>N: 3.94/3.67 | −42.0<br>c = 1.0 |

TABLE I-continued

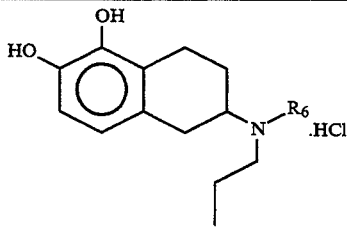

| Example | R$_6$ | Elemental Formula | Elemental Analysis (calc./obs.) | $[\alpha]_D$ (MeOH) |
|---|---|---|---|---|
| 12 | —CH$_2$CH$_2$—(tetrahydropyranyl) | C$_{20}$H$_{32}$NO$_3$Cl | C: 64.94/64.73<br>H: 8.72/8.58<br>N: 3.79/3.68 | −40.6<br>c = 1.4 |
| 13 | —(CH$_2$)$_3$OCH(CH$_3$)$_2$ | C$_{19}$H$_{32}$NO$_3$Cl | C: 63.76/63.60<br>H: 9.01/9.07<br>N: 3.91/3.89 | −47.4<br>c = 1.0 |
| 14 | —CH$_2$CH$_2$—(tetrahydrofuranyl) | C$_{19}$H$_{30}$NO$_3$Cl | C: 64.12/63.86<br>H: 8.50/8.69<br>N: 3.94/3.82 | −53.4<br>c = 1.1 |
| 15 | —CH$_2$—(tetrahydrofuranyl) | C$_{18}$H$_{28}$NO$_3$Cl | C: 63.24/63.18<br>H: 8.26/8.34<br>N: 4.10/3.92 | −53.6<br>c = 1.2 |

A similar procedure can be used to prepare compounds of the present invention wherein R$_3$ is H and R$_2$ is OH (general formula 2). This process is schematically described below (Method B), and in detail for Example #21.

Method B

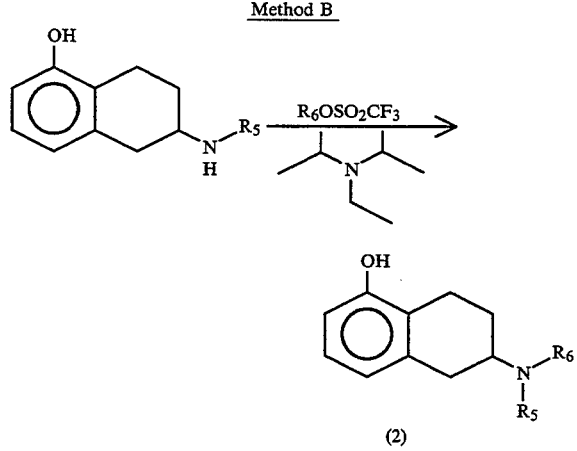

(2)

Method B - Detailed Example

Preparation of (6S)
-5,6,7,8-tetrahydro-6-[[(tetrahydro-3-furanyl) methyl ]propylamino]-1-naphthalenol, hydrochloride
(Example 21)

A.

(S)-5,6,7,8-Tetrahydro-6-propylamino-1-naphthalenol.

(S)-6-Propylamino-5,6,7,8-tetrahydro-1-naphthalenol, hydrobromide (3.5 g, 0.0122 mol, prepared as in Example 1, part A) was partitioned between concentrated ammonium hydroxide and ether. The layers were separated and the aqueous layer was extracted with ether. The combined organic layers were washed twice with water and once with saturated aqueous sodium chloride, dried (magnesium sulfate), filtered and concentrated to give 2.10 g of the free base (84% yield) as a white solid.

B.

(6S)-5,6,7,8-tetrahydro-6-[[(tetrahydro-3-furanyl)methyl]propylamino]-1-naphthalenol, hydrochloride.

A solution of tetrahydro-3-furanmethanol (0.37 g, 0.00362 mol) in methylene chloride (10 mL) was cooled in an ice-acetone bath with stirring under nitrogen. Diisopropylethylamine (0.94 g, 0.00727 mol) was added, followed by triflouromethanesulfonic anhydride (1.03 g, 0.00365 mol). The mixture was stirred for ten minutes, then a solution of (S)-5,6,7,8-tetrahydro-6-propylamino-1-naphthalenol (0.75 g, 0.00366 mol) in methylene chloride (15 mL) was added dropwise. The mixture was stirred at room temperature overnight. Water and ether were added, and the layers were separated. The ether layer was washed two times with water and once with a saturated aqueous sodium chloride, dried (magnesium sulfate) and concentrated. Column chromatography of the residue on silica eluting with ethyl acetate-light pet ether (1:4) afforded the oily free base of the product. The oil was dissolved in ether and treated with ethereal hydrogen chloride. The mother liquor was decanted from the amorphous solid which separated (alternatively, the solid can be collected by filtration), and the solid was dried under vacuum at 50° C. to give 0.43 g (36% yield) of product.

Table II summarizes compounds which are examples of the present invention prepared by Method B, in which R$_2$ is OH and R$_3$ is H:

TABLE II

[Structure: 5,6,7,8-tetrahydronaphthalen-1-ol with 2-position bearing N(R5)(R6)·HCl]

| Example | R5 | R6 | Empirical Formula | Elemental Analysis (calc./obs.) | $[\alpha]_D$ (MeOH) |
|---|---|---|---|---|---|
| 16 | —CH$_2$CH$_2$CH$_3$ | —(CH$_2$)$_2$—O—(cyclopentyl) | C$_{20}$H$_{32}$NO$_2$Cl | C: 67.87/67.65<br>H: 9.11/8.90<br>N: 3.96/3.94 | −52.9<br>(c = 1.0) |
| 17 | —CH$_2$CH$_2$CH$_3$ | —(CH$_2$)$_2$—O—(cyclopropyl) | C$_{18}$H$_{28}$NO$_2$Cl | C: 66.34/65.99<br>H: 8.66/8.44<br>N: 4.30/4.03 | −59.1<br>(c = 1.1) |
| 18 | —CH$_2$CH$_2$CH$_3$ | —(CH$_2$)$_2$—O—(cyclobutyl) | C$_{19}$H$_{30}$NO$_2$Cl | C: 67.14/67.38<br>H: 8.90/8.99<br>N: 4.12/4.07 | −56.4<br>(c = 1.4) |
| 19 | —CH$_2$CH$_2$CH$_3$ | —CH$_2$CH$_2$—(tetrahydrofuran-2-yl) | C$_{19}$H$_{30}$NO$_2$Cl<br>(½ H$_2$O) | C: 65.41/65.06<br>H: 8.96/8.56<br>N: 4.01/3.96 | −44.4<br>(c = 1.0) |
| 20 | —CH$_2$CH$_2$CH$_3$ | —CH$_2$—(tetrahydropyran-2-yl) | C$_{19}$H$_{30}$NO$_2$Cl | C: 67.14/66.94<br>H: 8.90/8.76<br>N: 4.12/3.89 | −52.9<br>(c = 1.0) |
| 21 | —CH$_2$CH$_2$CH$_3$ | —CH$_2$—(tetrahydrofuran-2-yl) | C$_{18}$H$_{28}$NO$_2$Cl | C: 66.34/66.25<br>H: 8.66/8.50<br>N: 4.30/4.19 | −56.9<br>(c = 1.0) |
| 22 | —CH$_2$CH$_2$CH$_3$ | —CH$_2$—(tetrahydrofuran-2-yl) | C$_{18}$H$_{28}$NO$_2$Cl | C: 66.34/66.20<br>H: 8.66/8.39<br>N: 4.30/4.22 | −55.9<br>(c = 1.1) |
| 23 | —CH$_2$CH$_2$CH$_3$ | —CH$_2$CH$_2$—(tetrahydropyran-2-yl) | C$_{20}$H$_{32}$NO$_2$Cl | C: 67.87/67.83<br>H: 9.11/8.77<br>N: 3.96/3.86 | −47.3<br>(c = 1.0) |
| 24 | —CH$_2$CH$_2$CH$_3$ | —CH$_2$CH$_2$—(tetrahydrofuran-2-yl) | C$_{19}$H$_{30}$NO$_2$Cl | C: 67.14/66.89<br>H: 8.90/8.69<br>N: 4.12/3.86 | −52.4<br>(c = 1.0) |
| 25 | —CH$_2$CH$_3$ | —CH$_2$CH$_2$—(tetrahydrofuran-2-yl) | C$_{18}$H$_{28}$NO$_2$Cl | C: 66.34/66.27<br>H: 8.66/8.86<br>N: 4.30/4.10 | −51.9<br>(c = 1.0) |

Compounds of the present invention wherein R$_2$ and R$_3$ are joined together to form the general structure (3) can be prepared as shown below (Method C). This process is described in detail for Example #26.

Method E

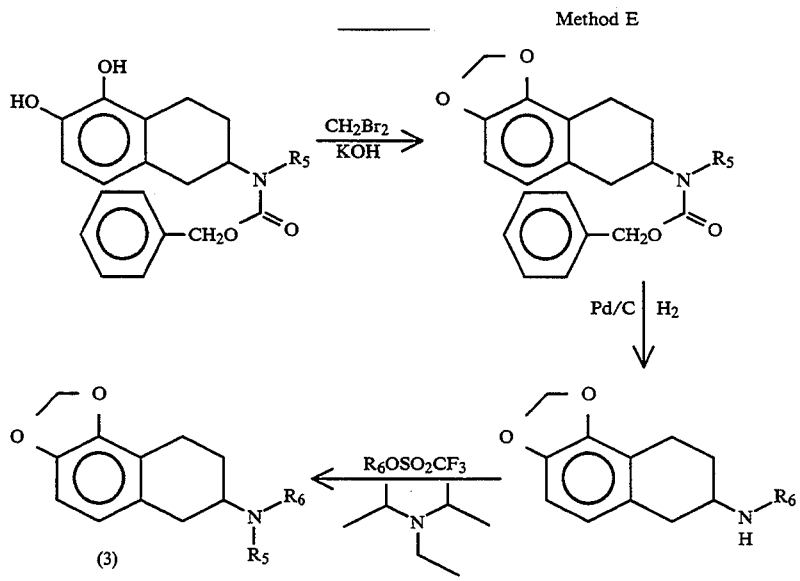

Method C - Detailed Example

Preparation of
(S)-6,7,8,9-tetrahydro-N-[2-(1-methylethoxy)ethyl]-N-propylnaphtho [1,2-d]-1,3-dioxol-7-amine, hydrochloride (Example 26)

A.

(S)-N-(6,7,S,9-Tetrahydronaphtho[1,2-d]1,3,dioxol-7-yl)N-propylcarbamic acid, phenylmethyl ester.

To a stirred suspension of potassium hydroxide (0.68 g, 0.0121 mol) in dimethyl sulfoxide (30 mL) under nitrogen was added a solution of (S)-N-(1,2,3,4-tetrahydro-5,6-dihydroxy-2-naphthalenyl)-N-propylcarbamic acid, phenylmethyl ester (1.5 g, 0.00422 mol, prepared as in Example 1, part D) in dimethyl sulfoxide (30 mL). The mixture was heated to 80° C. and dibromomethane (0.74 g, 0.00426 mol) was added. Heating was continued at 80° C. overnight, then the mixture was poured into dilute aqueous hydrochloric acid (600 mL). The resulting suspension was extracted with two portions of ether. The combined ether extracts layers were washed twice with water, twice with aqueous 5% sodium hydroxide, twice again with water and once with saturated aqueous sodium chloride, dried (magnesium sulfate), and concentrated. Column chromatography of the residue on silica eluting with ethyl acetate-light pet ether (1:9) afforded 1.14 g (74% yield) of product as a white solid.

B.

(S)-6,7.8.9-Tetrahydro-N-propylnaphtho[1,2-d]-1,3-dioxol-7-amine.

A solution of (S)-N-(6,7,8,9tetrahydron[1,2-d]-1,3-dioxol-7-yl)-N-propylcarbamic acid, phenylmethyl ester (1.14 g, 0.00311 mol) in tetrahydrofuran was shaken for one hour over 5% palladium on carbon under an initial pressure of 40 psi of hydrogen. The mixture was filtered to remove the catalyst, and the filtrate was concentrated. The oily product residue was used without additional purification.

C.

(S)-6,7,8,9-Tetrahydro-N-[2-(1-methylethoxy)ethyl]-N-propylnaphtho[1,2-d]-1,3-dioxol-7-amine, hydrochloride.

A solution of 2-(1-methylethoxy)ethanol (0.32 g, 0.00307 mol) in methylene chloride (10 mL) was cooled in an ice-acetone bath with stirring under a nitrogen atmosphere. Diisopropylethylamine (0.80 g, 0.00619 mol) followed by trifluoromethanesulfonic anhydride (0.88 g, 0.00312 mol) were added and the solution was stirred for five minutes. A solution of (S)-6,7,8,9-tetrahydro-N-propylnaphtho[1,2-d]-1,3-dioxol-7-amine (0.00311 mol) in methylene chloride (20 mL) was added and the mixture was stirred at room temperature overnight. Water and ether were added and the layers were separated. The organic layer was washed two times with water and once with saturated aqueous sodium chloride, dried (magnesium sulfate) and concentrated. Column chromatography on the residue on silica eluting with ethyl acetate-light pet ether (1:9) afforded the free base of the product as a colorless oil. The oil was dissolved in ether and treated with ethereal hydrogen chloride. The solvent was removed by distillation under reduced pressure (optionally decantation, or filtration) and the residue was dried under high vacuum at 40° C. to give 0.29 g (26% yield) of product.

Table III summarizes compounds which are examples of the present invention prepared by Method C, in which $R_2$ and $R_3$ are joined together to form the following structure:

TABLE III

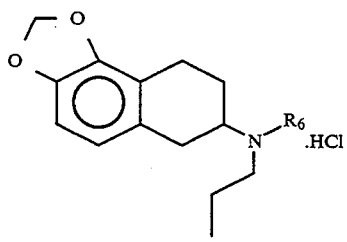

| Example | R6 | Empirical Formula | Elemental Analysis (calc./obs.) | [α]D (MeOH) |
|---|---|---|---|---|
| 26 | —(CH2)2OCH(CH3)2 | C19H30NO3Cl | C: 64.12/64.00<br>H: 8.50/8.59<br>N: 3.94/3.94 | −38.7<br>(c = 1.3) |
| 27 | —(CH2)2OCH2CH3 | C18H28NO3Cl | C: 63.24/63.00<br>H: 8.26/8.47<br>N: 4.10/3.98 | −51.8<br>(c = 1.2) |
| 28 | (CH2)2O(CH2)2CH3 | C19H30NO3Cl | C: 64.12/63.95<br>H: 8.50/8.63<br>N: 3.94/3.84 | −49.2<br>(c = 1.2) |
| 29 | —(CH2)2OC(CH3)3 | C20H32NO3Cl | C: 64.94/64.91<br>H: 8.72/8.57<br>N: 3.79/3.61 | −41.6<br>(c = 1.2) |

Compound of the present invention wherein A is:

(general formulae 4 and 5) can be prepared by the reaction of the phenolic compounds with an acyl chloride in the presence of a base as shown below (Method D). This process is described in detail for Examples #30 (R2 and R3=OA) and #37 (R2=OA, R3=H).

Method D

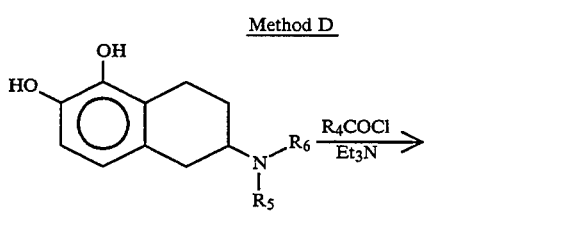

(4)

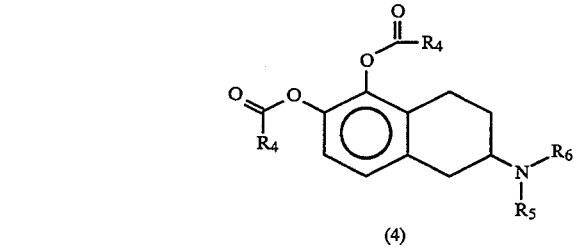

-continued
Method D

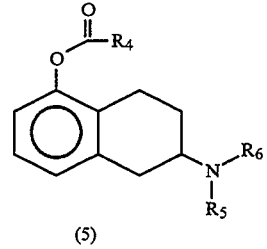

(5)

Method D - Detailed Example

Preparation of
(S)-5,6,7,8-tetrahydro-6-[[2-(1-methylethoxy)ethyl]-propylamino]-1,2-naphthalenediol, diaoetate (Example 30)

(S)-5,6,7,8-Tetrahydro-6-[[2-(1-methylethoxy)ethyl]-propylamino]-1,2-naphthalenediol (0.38 g, 0.00122 mol, free base prepared as in Example 1) was dissolved in methylene chloride (20 mL) with stirring in an ice bath under a nitrogen atmosphere. Triethylamine (0.28 g, 0.00277 mol) and acetyl chloride (0.20 g, 0.00255 mol) were added sequentially. The mixture was stirred at room temperature for three days. Water and ether were added and the layers were separated. The organic layer was washed once with water, once with aqueous saturated sodium bicarbonate, and once with aqueous saturated sodium chloride, then dried (magnesium sulfate) and concentrated. Column chromatography of the residue on silica eluting with ethyl acetate-light pet ether (2:3) gave 0.17 g (35% yield) of product.

Table IV summarizes compounds which are examples of the present invention prepared by Method D, in which R2 and R3 are OA, where A is:

TABLE IV

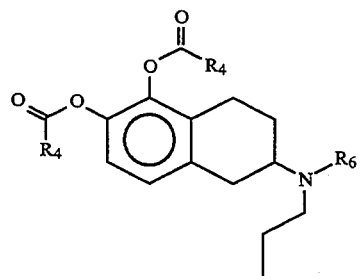

| Example | R$_4$ | R$_6$ | Empirical Formula | Elemental Analysis (calc./obs.) | $[\alpha]_D$ (MeOH) |
|---|---|---|---|---|---|
| 30 | —CH$_3$ | —(CH$_2$)$_2$OCH(CH$_3$)$_2$ | C$_{22}$H$_{33}$NO$_5$ | C: 67.49/67.39<br>H: 8.50/8.36<br>N: 3.58/3.41 | −40.1<br>(c = 0.73) |
| 31 | —(CH$_2$)$_4$CH$_3$ | —(CH$_2$)$_2$OCH(CH$_3$)$_2$ | C$_{30}$H$_{49}$NO$_5$ | C: 71.53/71.71<br>H: 9.81/10.00<br>N: 2.78/2.69 | −36.62<br>(c = 1.0) |
| 32 | —CH$_3$ | —(CH$_2$)$_2$O(CH$_2$)$_2$CH$_3$ | C$_{22}$H$_{33}$NO$_5$ | C: 67.49/67.70<br>H: 8.50/8.30<br>N: 3.58/3.54 | −46.9<br>(c = 0.67) |
| 33 | —CH$_3$ | —(CH$_2$)$_2$O(CH$_2$)$_3$CH$_3$ | C$_{23}$H$_{35}$NO$_5$ | C: 68.12/68.22<br>H: 8.70/8.52<br>N: 3.45/3.41 | −44.4<br>(c = 0.82) |
| 34 | —CH$_3$ | —(CH$_2$)$_2$OC(CH$_3$)$_3$ | C$_{23}$H$_{35}$NO$_5$ | C: 68.12/68.36<br>H: 8.70/8.83<br>N: 3.45/3.36 | −39.6<br>(c = 0.27) |
| 35 | —C(CH$_3$)$_3$ | —(CH$_2$)$_2$OCH(CH$_3$)$_2$ | C$_{28}$H$_{45}$NO$_5$ | C: 70.70/70.80<br>H: 9.54/9.54<br>N: 2.94/3.01 | −32.0<br>(c = 1.0) |
| 36 | —C(CH$_3$)$_3$ | —(CH$_2$)$_2$OC(CH$_3$)$_3$ | C$_{29}$H$_{47}$NO$_5$ | C: 71.13/70.89<br>H: 9.67/9.75<br>N: 2.86/2.87 | −29.9<br>(c = 1.5) |

Method D - Detailed Example

Preparation of (6S)-5,6,7,8-tetrahydro-6-[[2-(tetrahydro-2-furanyl)ethyl]propylamino]-1-naphthalenol, decanoate (Example 37)

A solution of (6S)-5,6,7,8-tetrahydro-6-[[2-(tetrahydro-2-furanyl)ethyl]propylamino]-1-naphthalenol (0.4 g, 0.00132 mol, free base prepared as in Example 30) and triethylamine (0.15 g, 0.00148 mol) in methylene chloride was stirred under nitrogen. Decanoyl chloride (0.28 g, 0.00147 mol) was added and the mixture was stirred at room temperature overnight. Water and ether were added and the layers were separated. The aqueous layer was extracted three times with ether, and the combined organic layers were washed with saturated aqueous sodium bicarbonate and with saturated aqueous sodium chloride, dried (magnesium sulfate) and concentrated. Column chromatography of the residue on silica eluting with ethyl acetate-light pet ether (3:7) gave 0.180 g (30% yield) of product.

Table V summarizes an example of the present invention prepared by Method D, in which R$_2$ is OA and R$_3$ is H, where A is:

TABLE V

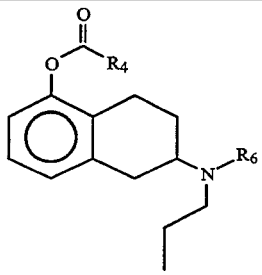

| Example | R4 | R6 | Empirical Formula | Elemental Analysis (calc./obs.) | $[\alpha]_D$ (MeOH) |
|---|---|---|---|---|---|
| 37 | —(CH$_2$)$_8$CH$_3$ | —CH$_2$CH$_2$—(tetrahydrofuran-2-yl) | C$_{29}$H$_{47}$NO$_3$ | C: 76.10/75.85<br>H: 10.35/10.04<br>N: 3.06/3.02 | −38.4<br>(c = 1.0) |

Compounds of the present invention wherein R$_2$ and R$_3$ are joined together to form the general structure (6) can be prepared as shown below (Method E). This process is described in detail in Example #38.

ride, dried (magnesium sulfate), treated with charcoal, and filtered. The filtrate was concentrated. Column chromatography of the residue on silica eluting with ethyl acetate-light pet ether (1:4) gave 1.04 g (49%

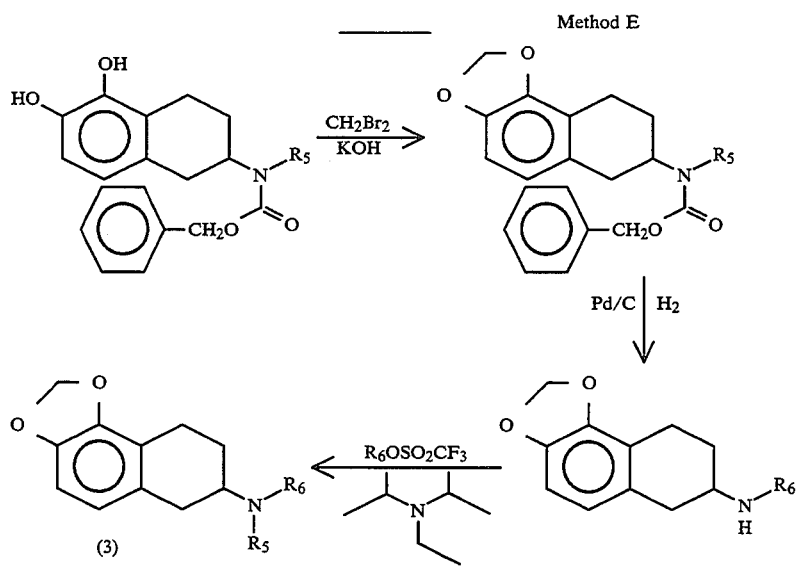

Method E

Method B - Detailed Example

Preparation of
(S)-5,6,7,8-tetrahydro-6-[[2-(1-methylethoxy)ethyl]-propylamino]-1,2-naphthalenediol, cyclic carbonate, hydrochloride (Example #38)

A.

(S)-N-(6,7,8,9-tetrahydro-2-oxonaphtho[1,2-d]-1,3-dioxol-7-yl)-N-propylcarbamic acid, phenylmethyl ester.

A solution of (S)-N-(1,2,3,4-tetrahydro-5,6-dihydroxy-2-naphthalenyl)-N-propylcarbamic acid, phenylmethyl ester (2.0 g, 0.00563 mol), phosgene (2.79 g of a 20% solution in toluene, 0.00558 mol) and triethylamine (1.70 g, 0.0168 mol) in methylene chloride (100 mL) was stirred overnight under nitrogen. The mixture was heated at reflux for one hour, cooled to room temperature, then water and ether were added. The layers were separated and the organic layer was washed twice with water and once with saturated aqueous sodium chloyield) of product.

B.

(S)-5,6,7,8-Tetrahydro-6-propylamino-1,2-naphthalendiol, cyclic carbonate.

A solution of (S)-N-(6,7,8,9-tetrahydro-2oxonaphtho[1,2-d]-1,3-dioxol-7-yl)-N-propylcarbamic acid, phenylmethyl ester (1.14 g, 0.00311 mol) in tetrahydrofuran was shaken for three hours over 5% palladium on carbon under an initial pressure of 40 psi of hydrogen. The mixture was filtered to remove the catalyst, and the filtrate was concentrated. The oily product residue was used without additional purification.

C.

(S)-5,6,7,8-Tetrahydro-6-[[2-(1-methylethoxy)ethyl]-propylamino]-1,2-naphthalenediol, cyclic carbonate, hydrochloride.

A solution of 2-(1-methylethoxy)ethanol (0.27 g, 0.00259 mol) in methylene chloride (10 mL) was stirred in an ice-acetone bath under a nitrogen and diisopropylethylamine (0.68 g, 0.00526 mol) followed by trifluoromethanesulfonic anhydride (0.74 g, 0.00262 mol) were added. The solution was stirred for ten minutes and a solution of (S)-5,6,7,8-Tetrahydro-6-propylamino-1,2-naphthalendiol, cyclic carbonate (0.00262 mol) in methylene chloride (10 mL) was added. The mixture was stirred overnight at room temperature. Water and ether were added and the layers were separated. The organic layer was washed once with water and once with saturated aqueous sodium chloride, dried (magnesium sulfate), filtered and concentrated. Column chromatography of the residue on silica eluting with ethyl acetate-light pet ether (1:4) gave the oily free base of the product. The oil was dissolved in ether and treated with ethereal hydrogen chloride and the solvent was removed under reduced pressure. The residual glass was washed twice with ether and the washings were decanted. Drying under high vacuum at 50° C. overnight gave 0.23 g (24% yield) of product.

Table VI summarizes an example of the present invention prepared by Method E, in which $R_2$ and $R_3$ are joined together to form the following structure:

TABLE VI

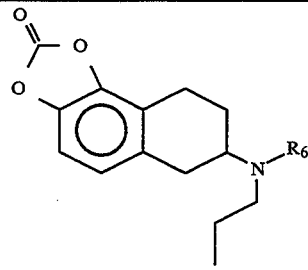

| Example | $R_6$ | Empirical Formula | Elemental Analysis (calc./obs.) | $[\alpha]_D$ (MeOH) |
|---|---|---|---|---|
| 38 | —(CH$_2$)$_2$OCH(CH$_3$)$_2$ | C$_{19}$H$_{28}$NO$_4$Cl | C: 61.70/61.49<br>H: 7.63/7.80<br>N: 3.79/3.65 | −49.8<br>(c = 0.57) |

PHARMACOLOGICAL TESTING OF EXEMPLIFIED COMPOUNDS

Pharmacological test methods are described below. The compounds of the present invention were tested for dopaminergic activity, with results being summarized in the accompanying tables. These data were generated to provide measures of the compounds' selectivity ($D_2/D_1$) for dopamine $D_2$ receptors, dopamine $D_2$ receptor in vitro functional potency and specificity ($D_2/\alpha_2$), as well as dopamine $D_2$ receptor in vivo functional potency. Test results for comparative examples in the prior art [see McDermed et al, J. Med. Chem., 19, 547 (1976); McDermed, et al, J. Med. Chem., 18, 362 (1975); Seiler, et al, J. Med. Chem., 29, 912 (1986)]are included for reference purposes [Example 39: 5-hydroxy-2-(di-n-propyl)aminotetralin, Example 40; (S)-5,6-dihydroxy-2-(di-n-propyl)aminotetralin, Example 41: (S)-5,6,7,8-tetrahydro-6-[(3-methoxypropyl)-propylamino]-1-naphthalenol].

1. Receptor Affinity Experiments (Radioligand Binding)

Membranes were prepared using a Brinkmann Polytron and collected by centrifugation. Membrane sources were bovine caudate ($D_2,D_1$) or rat cortex ($\alpha_2$). The membranes were washed, resuspended, and incubated at 37° C. for 30 min. in either the presence (rat cortex) of 1 $\mu$/ml adenosine deaminase or absence (bovine caudate) of 0.1 $\mu$/ml adenosine deaminase. Membranes were centrifuged, washed once and frozen at −70° C. until used. Immediately before use, the membranes were thawed, washed once, and resuspended to a final concentration of 0.5-2 mg/ml. Assays were initiated by addition of membranes. For $D_2$ and $D_1$ assays, the radioligands and conditions used were $^3$H-Spiperone (RT, 75 min.) and $^3$H-SCH23390 (37° C., 15 min.), respectively. For $\alpha_2$ assays, $^3$H-PAC (RT, 30 min.) was used Assays were terminated by filtration using a Brandel cell harvester over Whatman GF/B filters that had been pretreated with 0.1% polyethylenimine. The filters were counted in either a Beckman LS 3801 or TD 5000 scintillation counter. Data were analyzed using the Ligand program [Munson, P. and Rodbard, D., Analytical Biochemistry, 107, 220-239 (1980)]. The results are expressed in Table VII below:

TABLE VII

Dopamine $D_2$ and $D_1$ Receptor Affinity and Resultant Selectivity Ratio

| Example | $D_2K_1$ ($\mu$M) | $D_1K_1$ ($\mu$M) | Selectivity Ratio ($D_1 K_1/D_2 K_1$) |
|---|---|---|---|
| 1 | 0.065 | 7.24 | 112 |
| 2 | 0.316 | 6.31 | 20 |
| 3 | 0.065 | 4.79 | 74 |
| 4 | 0.363 | 7.08 | 19 |
| 5 | 0.115 | 4.57 | 40 |
| 6 | 0.051 | 5.01 | 98 |
| 7 | 0.129 | 4.68 | 36 |
| 8 | 0.112 | 5.89 | 52 |
| 9 | 0.054 | 8.91 | 166 |
| 10 | 0.054 | 2.45 | 46 |
| 11 | 0.030 | 4.27 | 141 |
| 12 | 0.025 | 5.49 | 224 |
| 13 | 0.051 | 5.75 | 113 |
| 14 | 0.195 | 6.61 | 34 |
| 15 | 1.100 | 1.100 | 1 |
| 16 | 0.062 | 7.94 | 129 |
| 17 | 0.468 | 9.77 | 21 |

TABLE VII-continued

Dopamine $D_2$ and $D_1$ Receptor Affinity and Resultant Selectivity Ratio

| Example | $D_2K_1$ ($\mu$M) | $D_1K_1$ ($\mu$M) | Selectivity Ratio ($D_1 K_1/D_2 K_1$) |
|---|---|---|---|
| 18 | 0.200 | 8.91 | 45 |
| 19 | 0.110 | 1.51 | 14 |
| 20 | 1.070 | 7.08 | 7 |
| 21 | 0.151 | 3.63 | 24 |
| 22 | 1.510 | 16.2 | 11 |
| 23 | 0.110 | 7.41 | 68 |
| 24 | 0.263 | 5.62 | 21 |
| 25 | 0.117 | 6.61 | 57 |
| 39 | 0.790 | 3.80 | 5 |
| 40 | 0.115 | 1.29 | 11 |
| 41 | 0.790 | 11.0 | 14 |

These data show the high degrees of dopamine $D_2$ receptor affinity and selectivity achieved with compounds of the current invention.

2. Dopamine - $D_2$ In Vitro Functional Test

Vasa deferentia from male BALB/C mice weighing approximately 30 g were removed and placed in isolated organ baths containing magnesium-free modified Krebs-Henseleit solution which was gassed with 95% $O_2$ and 5% $CO_2$ and maintained at 37° C. Tissues were set up under resting tension of 0.5 g and stimulated electrically at 60 volts, 0.1 Hz and 1 msec duration to produce a series of twitch responses. Tissues were pretreated with propranolol (1 $\mu$M) to block $\beta$-adrenoceptors, idazoxan (3 $\mu$M) to block $\alpha_2$-adrenoceptors receptors, and ascorbic acid (100 $\mu$M) for 60 min before the addition of test compound. The potency of the test compound is expressed as the concentration that produces 50% of the maximal inhibition of twitch. These results are summarized in Table VIII below.

3. Adrenergic - $\alpha_2$ In Vitro Functional Test

Vasa deferentia from male Sprague-Dawley rats weighing between 150-250 g were removed and placed in isolated organ baths containing Krebs-Henseleit solution under a resting tension of 1 g. All other set up conditions were identical to those used for the mouse was deferens. Tissues were pretreated with propranolol (1 $\mu$M), ascorbic acid (100 $\mu$M) and the $\alpha_1$-adrenergic antagonist prazosin (0.3 or 1 $\mu$M) for 60 min before the addition of test compound. The potency of the test compound is expressed as the concentration that produces 50% of the maximal inhibition of twitch. These results are summarized in Table VIII below.

TABLE VIII

Functional Potencies at $D_2$, $a_2$ Receptors and Resultant Specificity Ratio

| Example | $D_2 A_{50}$ (nM) | $a_2 A_{50}$ (nM) | Specificity Ratio ($a_2 A_{50}/D_2 A_{50}$) |
|---|---|---|---|
| 1 | 0.148 | 218 | 1480 |
| 2 | 0.417 | 18.6 | 45 |
| 3 | 0.105 | 195 | 1860 |
| 4 | 0.603 | 42.7 | 71 |
| 5 | 0.240 | 245 | 1020 |
| 6 | 0.162 | 87.1 | 537 |
| 7 | 0.794 | 148 | 186 |
| 8 | 0.269 | 107 | 398 |
| 9 | 0.089 | 144 | 1620 |
| 10 | 0.093 | 93.3 | 1000 |
| 11 | 1.290 | 79.4 | 62 |
| 12 | 0.200 | 199 | 1000 |
| 13 | 0.102 | 93.3 | 914 |
| 14 | 0.209 | 14.8 | 71 |
| 15 | 0.141 | 16.6 | 118 |
| 16 | 0.513 | >10000 | >19500 |
| 17 | 0.589 | >10000 | >17000 |
| 18 | 0.676 | >10000 | >14800 |
| 19 | 0.275 | 1740 | 6310 |
| 20 | 1.000 | 190 | 191 |
| 21 | 0.977 | 275 | 282 |
| 22 | 2.190 | 3550 | 1620 |
| 23 | 0.437 | >10000 | >22900 |
| 24 | 0.776 | 123 | 158 |
| 25 | 0.708 | >10000 | >14100 |
| 39 | 2.140 | 257 | 120 |
| 40 | 0.250 | 12.5 | 50 |
| 41 | 0.910 | 234 | 257 |

These data show the high degrees of dopamine $D_2$ receptor in vitro functional activity and specificity ($D_2$ vs. $\alpha_2$). See U.S. Pat. No. 5,068,325, which explains the importance of high degrees of $D_2$ vs. $\alpha_2$ specificity.

4. In Vivo Functional Test

Dopamine agonists produce contralateral circling behavior in rats in which unilateral lesions of the substantial nigra are made by prior injection of 6-hydroxydopamine. The circling is thought to be mediated by stimulation of denervated supersensitive postsynaptic dopamine receptors (Marshall and Ungerstedt, 1977, Eur. J. Pharmacol., 41:361-367). The method of Van der Werf, et al. (Eur. J. Pharmacol., 102:387-399) was used, and the results are summarized in Table IX below.

TABLE IX

In Vivo Functional Potencies

| Example | $ED_{50}$ ($\mu$mol/kg) |
|---|---|
| 1 | 0.004 |
| 2 | 0.004 |
| 3 | 0.007 |
| 4 | 0.006 |
| 5 | 0.006 |
| 6 | 0.008 |
| 7 | 0.002 |
| 8 | 0.004 |
| 9 | 0.004 |
| 10 | 0.030 |
| 11 | 0.010 |
| 12 | 0.030 |
| 13 | 0.006 |
| 14 | 0.030 |
| 15 | 0.009 |
| 16 | 0.090 |
| 17 | 0.009 |
| 18 | 0.020 |
| 19 | 0.020 |
| 20 | 0.030 |
| 21 | 0.009 |
| 22 | 0.030 |
| 23 | 0.010 |
| 24 | 0.020 |
| 25 | N/A |
| 26 | 0.030 |
| 27 | 0.100 |
| 28 | 0.100 |
| 29 | 0.040 |
| 38 | 0.005 |
| 39 | 0.010 |
| 40 | 0.009 |

TABLE IX-continued

| | In Vivo Functional Potencies |
|---|---|
| Example | ED$_{50}$ ($\mu$mol/kg) |
| 41 | 0.020 |

These data show the high degrees of dopamine D$_2$ receptor functional potencies achieved with the compounds of the present invention.

Having now described the invention, I claim:

1. Optically active or racemic compounds represented by the formula:

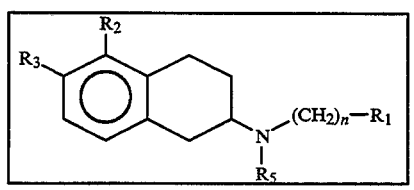

wherein R$_1$ is alkoxy selected from the group consisting of ethoxy, propoxy, isopropoxy, butoxy, s-butoxy, isobutoxy and t-butoxy; cycloalkoxy; or a cyclic ether of the formula:

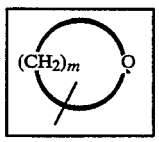

where m is an integer from 3 to 5;
R$_2$ is OA; R$_3$ is selected from the group consisting of H and OA; where A is H or is selected from the group consisting of hydrocarbyl radicals having from 1 to 3 carbon atoms,

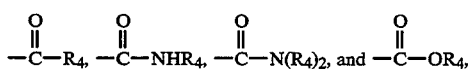

with the proviso that when R$_1$ is alkoxy, then R$_3$ cannot be H, and with the further proviso that when both R$_2$ and R$_3$ are OA, then R$_2$ and R$_3$ may be bonded together to form the group

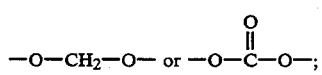

R$_4$ is selected from the group consisting of alkyl and aromatic residues having from 1 to 20 carbon atoms; n is an integer from 1 to 4; and R$_5$ is an unbranched alkyl chain having from 1 to 3 carbon atoms or a cyclopropylmethyl radical.

2. The compounds of claim 1 wherein A is H.
3. The compounds of claim 1 wherein A is selected from the group consisting of hydrocarbyl radicals having from 1 to 3 carbon atoms.
4. The compounds of claim 1 wherein A is selected from the group consisting of

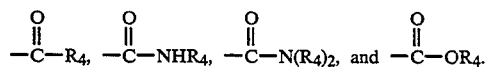

5. The compounds of claim 4 wherein R$_4$ is selected from the group consisting of alkyl radicals.
6. The compounds of claim 2 wherein R$_1$ is selected from the group consisting of ethoxy, propoxy, isopropoxy, n-butoxy, t-butoxy, s-butoxy, isobutoxy, and tetrahydro-3-furanyl.
7. The compounds of claim 2 wherein R$_3$ is H.
8. The compounds of claim 2 wherein R$_3$ is OA.
9. The compounds of claim 8 wherein A is selected from the group consisting of H,

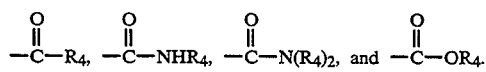

10. The compounds of claim 8 wherein R$_2$ and R$_3$ are taken together to form the group

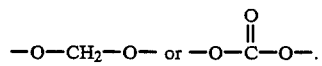

11. The compounds of claim 6 wherein n is 2.
12. The compounds of claim 11 wherein R$_3$ is OA.
13. The compounds of claim 12 wherein R$_1$ is selected from the group consisting of isopropoxy and t-butoxy.
14. The compounds of claim 13 wherein the optically active compound is the S-enantiomer.
15. A method for inducing a dopaminergic response in a mammal comprising administering to said mammal an effective mount of a compound selected from the group consisting of a compound represented by the formula

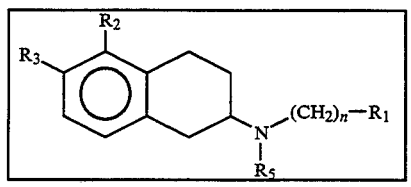

wherein R$_1$ is alkoxy selected from the group consisting of ethoxy, propoxy, isopropoxy, butoxy, s-butoxy, isobutoxy and t-butoxy; cycloalkoxy; or a cyclic ether of the formula

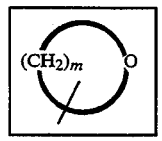

where m is an integer from 3 to 5;
R$_2$ is OA; R$_3$ is selected from the group consisting of H and OA; wherein A is H or is selected from the group consisting of hydrocarbyl radicals having from 1 to 3 carbon atoms,

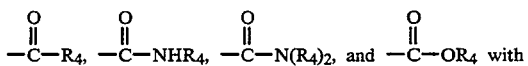

the proviso that when $R_1$ is alkoxy, then $R_3$ cannot be H, and with the further proviso that when both $R_2$ and $R_3$ are OA, then $R_2$ and $R_3$ may be bonded together to form the group

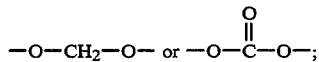

$R_4$ is selected from the group consisting of alkyls and aromatic residues having from 1 to 20 carbon atoms; n is an integer from 1 to 4; and $R_5$ is an unbranched alkyl chain having from 1 to 3 carbon atoms or a cyclopropylmethyl radical.

16. The method of claim 15 wherein $R_3$ is H.
17. The method of claim 15 wherein $R_3$ is OA, and A is selected from the group consisting of H and

18. The method of claim 17 wherein $R_4$ is selected from the group of alkyl radicals.
19. The method of claim 18 wherein n is 2.
20. The method of claim 19 wherein $R_1$ is selected from the group consisting of isopropoxy and t-butoxy.
21. The method of claim 20 wherein the optically active compound is the S-enantiomer.

* * * * *